US006845327B2

(12) United States Patent
Lauks

(10) Patent No.: US 6,845,327 B2
(45) Date of Patent: Jan. 18, 2005

(54) POINT-OF-CARE IN-VITRO BLOOD ANALYSIS SYSTEM

(75) Inventor: Imants R. Lauks, Ottawa (CA)

(73) Assignee: Epocal Inc., Ottawa (CA)

(*) Notice: Subject to any disclaimer, the term of this patent is extended or adjusted under 35 U.S.C. 154(b) by 536 days.

(21) Appl. No.: 09/875,949

(22) Filed: Jun. 8, 2001

(65) Prior Publication Data

US 2003/0148530 A1 Aug. 7, 2003

(51) Int. Cl.[7] .................................................. G01N 1/00
(52) U.S. Cl. ........................................................ 702/23
(58) Field of Search .......................... 702/23; 600/453, 600/437, 18, 492, 322, 547, 455; 324/71, 103; 356/36, 601; 607/5, 60; 225/778; 436/63; 435/18; 367/135; 73/625, 54; 377/12, 10

(56) References Cited

U.S. PATENT DOCUMENTS

| | | | |
|---|---|---|---|
| 4,149,405 A | * | 4/1979 | Ringrose .................... 73/54.01 |
| 4,342,964 A | | 8/1982 | Diamond et al. |
| 4,734,184 A | | 3/1988 | Burleigh et al. |
| 5,096,669 A | | 3/1992 | Lauks et al. |
| 5,124,661 A | | 6/1992 | Zelin et al. |
| 5,282,950 A | | 2/1994 | Dietze et al. |
| 5,628,961 A | | 5/1997 | Davis et al. |
| 5,781,024 A | | 7/1998 | Blomberg et al. |
| 5,829,950 A | | 11/1998 | Alder |
| 6,011,985 A | * | 1/2000 | Athan et al. ................ 600/322 |
| 6,066,243 A | | 5/2000 | Anderson et al. |
| 6,066,504 A | * | 5/2000 | Jina ............................ 436/69 |

FOREIGN PATENT DOCUMENTS

| | | |
|---|---|---|
| WO | WO 97/08544 | 3/1997 |
| WO | WO 98/37804 | 9/1998 |
| WO | WO 99/00667 | 1/1999 |
| WO | WO 00/21434 | 4/2000 |

OTHER PUBLICATIONS

International Fed. Clinical Chem., Proceedings of the 17th International Symposium, Nice, France Jun. 1998, eds. P. D'orazio, N. Fogh–Andersen and L. Larsson, Omnipress, Madison, WI USA, 1998. pp 3–15.

* cited by examiner

*Primary Examiner*—John Barlow
*Assistant Examiner*—Tung S Lau
(74) *Attorney, Agent, or Firm*—L. Anne Kinsman; Borden, Ladner, Gervais LLP

(57) ABSTRACT

Devices for cost-effectively performing in-vitro diagnostic chemical analyses at multiple distributed locations within a medical institution are disclosed. One object of this invention is to provide a network of distributed sensory devices that acquire sensor signals from blood specimens and deliver those signals through a connect on to a central location for analysis by a general-purpose computer and generation of an analysis result. The analysis result is then sent to numerous locations on a network for display, including also possibly back to the location of signal acquisition. Cost-effective mobile sensing devices are also disclosed. The present system includes blood-sensor signal acquisition devices distributed throughout the hospital. The sensory signal-acquisition devices are card readers that acquire raw sensory signals from diagnostic cards inserted therein. These diagnostic cards are smart card-like devices modified for blood collection that contain sensory elements such as electrodes adapted to provide a raw sensory signal. The signal acquisition devices are modified smart card readers, which acquire the raw sensory data from an inserted smart card through a standardized contact arrangement and provide the raw data to data processing devices such as data acquisition cards. The system includes multiple remote ports for acquiring blood sensor signals. One or more card reader, when connected to a mobile general-purpose computer, can be converted into a complete mobile blood analyzer.

31 Claims, 5 Drawing Sheets

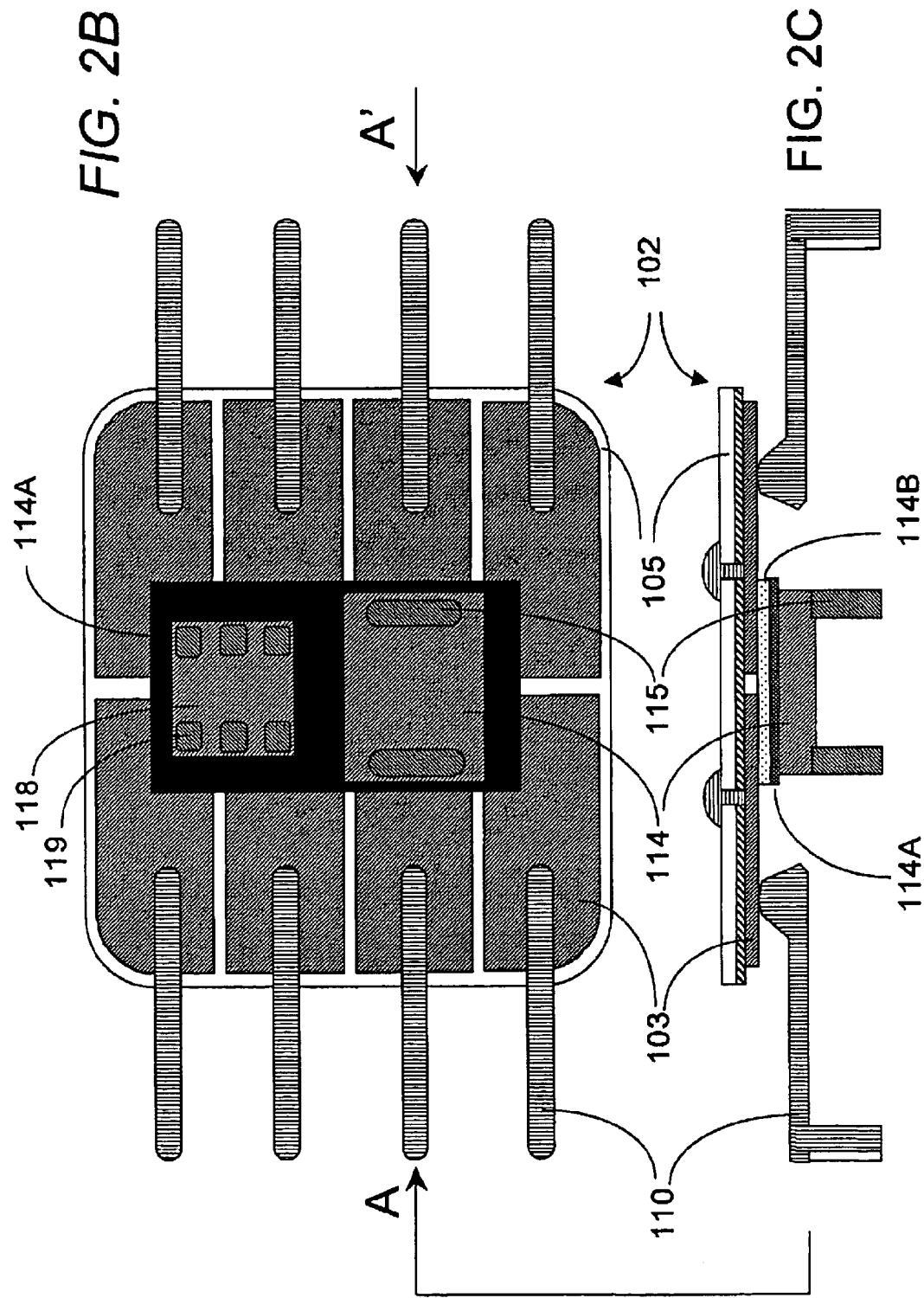

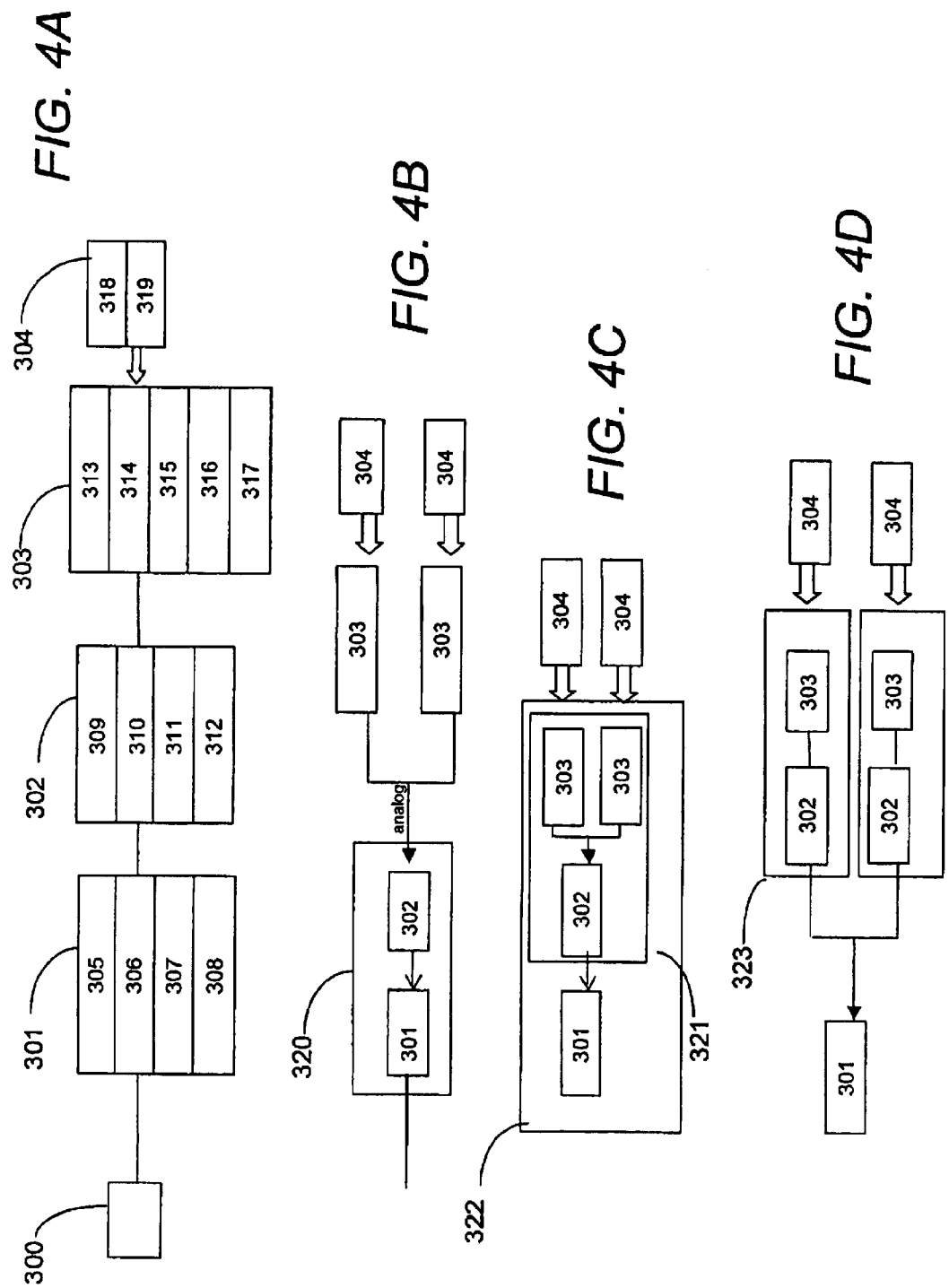

POINT-OF-CARE IN-VITRO BLOOD ANALYSIS SYSTEM

FIELD OF THE INVENTION

This invention is directed to instrumentation for cost-effective in-vitro blood analysis at the point of care.

BACKGROUND OF THE INVENTION

Distributed in-vitro blood analysis within a hospital is also known as point-of care, bedside or patient-side testing. In the hospital point-of-care measurement art a typical installation consists of an array of blood analysis instruments in multiple remote locations. Point-of-care in-vitro blood analysis instruments of the prior art perform measurements of blood chemical concentrations on discrete blood specimens. A very typical example might be a hospital consisting of numerous medical units containing patient beds. In such a measurement application blood analysis instrumentation is placed at or near-patient locations, i.e. at the point-of-care, such as in the unit or even at the patient bedside. Instruments are sometimes placed at fixed locations, other times they are portable. There are of course also blood analysis instruments within the hospital's centralized blood testing laboratory.

The value of point-of-care blood analysis is derived from the improved medical outcomes and operational convenience of fast turnaround time of results, as compared to the much longer turnaround time of results from a remote central laboratory. However such improved service to be economical cannot come at a cost per blood analysis much higher than the cost of the service from the laboratory. The cost per blood analysis (commonly referred to as cost per test) of a point-of-care measurement is given by the total equipment cost per test (daily capital depreciation and maintenance cost divided by the number of blood analyses or tests per day) plus the cost per test of disposable components or test consumables. However, since the testing frequency per patient location is low, no economies of scale can be realized so that the capital cost of bedside units must be kept low, if the point-of-care costs per analysis are to be maintained at or below the cost of testing in the lab. Despite this basic requirement, prior are point-of-care blood analysis systems are only available at high unit cost which most of the time renders the use of one unit per bedside completely uneconomical. To remedy this situation, prior art units are shared among numerous beds, creating an additional set of problems associated with the need for safe transportation and movement of expensive instrumentation within the hospital environment and constant monitoring and management of the equipment's availability. In the alternative, one expensive analyzer is placed in a laboratory site within the unit or in a satellite stat laboratory close to the unit and serves an entire medical unit's blood testing needs with the patient blood samples being transported to it. This reduces cost per test, because the capital cost for the expensive analyzer is divided over a large test volume, but the associated increase in turnaround time and decreased operational convenience significantly diminishes the point-of-care value proposition. Thus, there exists a need for low cost bedside units for point-of-care analysis.

Conventional point-of-care blood analysis instrumentation is always in the form of a complete or nearly complete analyzer. It is capable on its own to deliver an analysis result (for example a blood concentration value) rather than just a raw sensor output. Although the array of point-of-care instruments in a hospital-wide installation often communicates analysis results (blood concentration data) to a central, general-purpose computer, that computer is simply used for centralized collection and aggregation of analysis results and other patient relevant data, but not for sensory signal analysis. That is generally carried out in the conventional self-contained point-of-care analyzer instrumentation.

Point-of-care blood analyzers include devices for both quantitative and qualitative blood measurements and generally include complex and expensive hardware as well as all of the measurement software required for complete analysis. Thus, a complete analyzer is provided at each measurement location, which results in high operating cost for the conventional system even when the analyzer units are shared among numerous beds.

Prior-art blood analyzers, particularly those for quantitative blood analysis, consist of numerous electronic components. There are blood sensors connected to signal conditioning amplifiers and filters, then digitization circuits. Digital signals are transferred to microprocessor and memory units contained within the analyzer. The microprocessor accepts the sensor signals and uses the internal software to calculate concentration values, i.e. the final analysis result. In these self-contained analyzers of the prior art, microprocessors and their software also control the measurement process itself by controlling fluidic processes, the temperature of the measurement chamber and quality control processes. They also control a display that outputs the calculated concentration value contained within the analyzer memory. The microprocessor further controls the transmission of the analysis result, and possibly the measurement parameters to a other devices such as a central data station. The central data station can be a general-purpose computer, located for example in the central laboratory, or it may be at a port on a network such as the hospital information system or the laboratory information system.

In a typical hospital installation there are numerous point-of-care blood analyzer instruments connected to a central data station in which the point-of-care blood analysis data is aggregated. That data is consolidated with other point-of-care data from other devices in the hospital's laboratory information system. The centralized data is used for archiving purposes, for patient billing as well as for quality assurance.

In prior-art point-of-care blood analyzers, particularly in quantitative analyzers with laboratory grade accuracy, the sensors and related measurement hardware are complex and expensive. Some sensors cannot be re-used and are thus particularly expensive, or if they are re-usable, mast be washed between uses adding cost to the fluidics hardware described below. Moreover, the sensors' output is often not simply related to concentration and the relationship is not fixed over time. Thus, sensors can require frequent calibration. Sensors are used in a discrete sampling manner rather than in an in-line continuous measurement manner. To perform the required discrete sample acquisition step, as well as the necessary sensor calibration and washing steps and addition of other reagents if required the analyzer includes fluidic elements. The fluidics hardware consists of a measurement chamber containing sensors, orifices and conduits for introduction and movement of fluids, reagent reservoirs, waste chambers and the like. The fluids are actuated by often complex and costly electromechanical components such as pumps and valves. U.S. Pat. No. 4,734,184 describes a typical example of prior-art fluidics in a point-of-care sensor system with reusable sensors, while U.S. Pat. Nos. 4,342,964 and 5,096,669 describe fluidics for unit-use disposable devices. The blood analysis procedure typically also requires control of the measurement temperature and sometimes gas pressures. This and other related measurement hardware, particularly in optical measurement technology, can also be expensive. In total these various complicating elements of prior-art point-of-care blood analyzers add significant cost to each device. Even if much of the electronic hardware and software were to be stripped out of a defeaturized point-of-care analyzer of prior art design there would still be significant other remaining cost of sensors and measurement hardware contained within the device. Thus, there has heretofore been limited financial incentive to try to simplify electronic hardware and software.

What increases the cost of current point-of-care analysis even more is the use of numerous instruments at a typical bedside location in a hospital for monitoring the patient's status. These include biochemical measurement devices such as point-of-care blood analyzers and physical monitoring devices such as patient monitors. There may be numerous different types of in-vitro blood analyzers at each point-of-care location. For example, there may be an analyzer to measure glucose, another to measure blood gases and still others to measure blood coagulation, cardiac markers and so on. Each of these conventional devices is a self-contained analyzer. Thus an instrumented bedside is not only crowded but consists of significant and often duplicated hardware associated with significant capital cost.

Attempts to integrate technologies into simpler, more consolidated point-of-care tools have included the modular approach described below with respect to the Diametrics and Agilent instruments. A different approach has been to design completely new instruments combining the different measurement technologies. But such redesigns are expensive and add to the cost of the final device. In summary, integration of prior art point-of-care medical equipment has proven difficult and the resulting devices are still very complex and therefore expensive.

One concept intended to address this problem is the approach of providing modules or defeaturized medical instrumentation for connection to other instruments. For example, the concept was discussed in "Internat. Fed. Clinical Chem., Proceedings of the 17th International Symposium, Nice, France June 1998, eds. P. D'oruzio, N. Fogh-Andersen and L. Larsson, Omnipress, Madison, Wis. USA, 1998. pp3–15. A defeaturized blood-analysis device configured as a modular subsystem of a complete blood analyzer is described in U.S. Pat. No. 6,066,243 to Diametrics. Blood analysis devices that are modular components of a patient-monitoring system are marketed by Agilent Technologies. Though these prior-art defeaturized devices have less hardware than a self-contained analyzer, they still contain many of the components of a complete analyzer. The commercial blood-analysis modules of the prior art contain at least a micro-processor unit and software for calculation of a concentration value from raw sensor signals and for control of the measurement process, quality assurance testing and thermal control. Prior-art modules also still contain complex electromechanical subsystems for driving the analyzer's fluidics. Moreover, the defeaturized devices of the above-cited prior art are intended for incorporation into the housing of a parent instrument, together again forming a completely self-contained bedside in-vitro blood analyzer. That parent instrument in turn is a special-purpose device not a general-purpose device which could be used with many modules. Thus even these attempts at defeaturization of the measurement devices of the prior art thus far have required much costly, specialized hardware at each measurement location. Thus, mere still exists a need for a low cost bedside instrumentation alternative.

Clinical laboratory regulations require hospitals to perform intermittent verification of the integrity of their blood analyzers. Hospitals administrators have also developed quality control protocols for verification of the proper function of their blood analyzers at the point of care. It is well known in the art of quality control that quality systems should effectively expose non-conformance in those elements of the instrument that are most likely to give error during use. Traditional laboratory quality control protocols have included measurements with the analyzer of liquid samples of known concentration. In point-of-care systems and especially in systems employing unit-use diagnostic devices various components of the sensor signals (signal levels and drift rate, noise level) are used to indicate non-conforming performance of the sensor and fluidics. Also, manufacturers have provided electronic devices that have been designed for use in checking the integrity of the electronics, software and electromechanical subsystems of the analyzer. The prior art contains examples of different configurations of electronic testers that have been useful in controlling point-of-care analyzers. U.S. Pat. No. 5,124,661 for example discloses an electrical test head for connection to a blood analyzer. The electrical test head plugs into the analyzer's sensor card connector and simulates the electrical outputs of a sensor card. U.S. Pat. No. 5,781,024 describes an instrument performance verification system. This patent describes a portable analyzer for contacting to a sensor card, the analyzer containing measuring circuitry and electrical verification circuitry within the single portable housing. U.S. Pat. No. 5,829,950 also discloses an electrical integrity test circuit internal to the instrument.

Another disadvantage of conventional distributed self-contained point-of-care devices resides in the quality assurance problem they present. Because they are self-contained analyzers they incorporate a fall suite of software to manage all aspects of the blood analysis. It is often the case that manufacturers issue new versions of software to update an analyzer to a new revision. This might be to enable new blood tests, or to provide better measurement algorithms to obtain more accurate results or to provide for correction factors if the calibration of manufactured batches of sensors or reagents have changed. A hospital installation that might comprise numerous (sometimes hundreds) such analyzers, each with its own software, can become a serious quality assurance problem in this kind of environment. This problem is compounded by the fact that at each point of care there may be analyzers from several manufacturers using very different measurement technologies, each analyzer having a full suite of software with several versions coexisting at one time. The professionals responsible for quality assurance of distributed instrumentation software in a chaotic environment such as a hospital recognize this to be a significant problem.

There remains a significant need in the field of healthcare to provide an improved point-of-care blood measurement system, that is both cost-effective and addresses problems of quality assurance in remote testing. The devices of the present invention address that need.

Distributed sensors for the production of sensory data are not used in the hospital environment. Although distributed sensors are known in an industrial setting, also known as all enterprise measurement system, they are not part of a smart card/card reader/general purpose computer combination. In contrast, in the industrial measurement art a typical installation consists of an array of sensors installed at multiple remote locations and connected to a central computer for data acquisition. A very typical example might be a chemical plant in which chemical processes occur in reactors connected by pipes. In such a typical measurement application, the factory engineers have found it necessary to measure quantities such as temperature, flow rate, acidity and dissolved oxygen at numerous different locations within the chemical plant. The engineers have installed these sensors in the various remote locations within pipes and reaction vessels. Electrical signals from sensors of this prior art are typically low-level outputs in the milli-volt range at high impedance from voltage generating sensors or micro-amp currents from current generating sensors. As such they are prone to pick up noise during transmission. Thus, each sensor is connected to a signal-conditioning device placed in close proximity to the sensor. The signal-conditioning device converts the raw electrical output from the sensor to a more robust signal that can be transmitted from the sensing location. Such a signal-conditioning device might be simply analog signal amplification and noise filtering circuitry when it is appropriate to transmit an analog level. Interposed between the central computer and the remote sensors and signal-conditioning device is a data acquisition interface. This device contains signal conversion circuitry and digital and/or analog input/output (I/O) circuits. The signal conversion circuitry digitizes the analog sensor signal and converts it into one of several digital data stream formats. Conditioned analog sensor signals can be converted by a data acquisition interface installed in the computer when the distance between remote sensors and computer is short. Such a device is called a data acquisition (DAQ) card. For long distances it is appropriate to install the data acquisition interface with signal conversion structure close to the sensor site. Such a conversion device might then digitize the sensor signal and convert it to one of several data stream transmission protocols such as RS232. As is known in the art it is also now feasible to transmit the data stream from the remote sensor to the central computer by either a wire connection or by radio waves over a wireless connection.

In the industrial measurement applications sensors generally deliver signals that are directly related to the concentration value through a fixed calibration factor. The calibration factor is constant over numerous measurements. The sensors thus do not need calibration at each use occasion. There is no requirement to wash and otherwise prepare the sensor for a new measurement. Sensors are used in a continuous in-line measurement situation rather than a discrete sampling application. Sensors in a continuous-monitoring biomedical application also resemble the above characteristics of industrial sensors. Manufacturers have developed general-purpose measurement and control devices to cost-effectively serve this industrial sensor market application. Thus devices such as general-purpose signal conditioning modules are available as articles of commerce. Data acquisition interfaces such as general-purpose DAQ cards, and I/O devices with RS232 transmitters or with radio frequency links are now all available as articles of commerce. The use of such general-purpose devices is well established in the prior art of industrial sensing. W.O. Pat. Nos. 9837804 and 0021434 disclose a modular measurement device for biomedical continuous monitoring sensors. These patents disclose an integrated element for connection to a general-purpose computer consisting of a DAQ PC card containing a sensor.

SUMMARY OF THE INVENTION

It is now an object of the present invention is to provide an improved system for point-of-care in-vitro blood measurement.

It is another object to provide a point-of-care blood measuring system that includes low cost bedside components including only a minimum of hardware.

It is still a further object to provide a point-of-care blood measuring system which requires as little electrical, electromechanical and electronic hardware as possible at each blood measurement location, yet sacrifices none of the performance attributes of a self-contained analyzer at that location.

These and other objects which will become apparent below are met by a system consisting of at least one card reader for receiving a raw sensor signal from a diagnostic card, and for connection to a single general-purpose computer through a data acquisition interface. The diagnostic card reader and the companion unit-use diagnostic cards are preferably based on modified smart-card technology. Cards and card readers are compact in size and very inexpensive to produce. Diagnostic cards are modified smart cards that incorporate a blood collection structure and low cost electrochemical sensor arrays and fluidic components, as described briefly below and in detail in co-pending patent application Ser. No. 09/871,821. Sensor arrays are produced on smart-card chip modules adapted for use as electrochemical electrodes. The diagnostic card with its chip module is preferably constructed with materials and geometries that conform to ISO standards established for electronic smart cards. In use, the diagnostic cards are intended to engage with a set of connectors for transferring the sensor's raw electrical sensor signals from the card to the card reader device.

A card reader according to this invention preferably includes one or more connectors for engagement with a contact arrangement on the unit-use diagnostic cards, a signal amplification circuit and optional multiplexing and signal filtering circuits, and a thermal sensor and heater. The card reader is preferably a modified conventional smart-card connector with an electrical circuit board mounted thereon. The smart-card connector modification includes a thermal sensor and heater housed in the connector, positioned so as to effect contact with the card in the measurement region and optional other minor modifications to accommodate the diagnostic card's fluidics.

In keeping with the basic principle of the invention to provide a system with low cost distributed components, the card readers do not contain microprocessors and software for calculating analysis results or converting sensor signals to blood concentration data, for thermal control, for control of the measurement process, or for quality control. These items are contained in the general-purpose computer to which the readers are connected. Thus, the costly signal analysis components which are duplicated in each conventional analyzer are provided only once in the system in accordance with the invention, namely in the general purpose computer. Preferably, the card readers also do not contain complex electromechanical components.

Within the framework of this invention, the term general purpose computer is intended to include any general purpose computing device capable of carrying out the analysis function fully or in combination with other computing devices linked therewith, such as for example in a network. Thus, the term is intended to cover, among others, PCs, laptops, networks, servers on a private or public network, servers accessible through the internet, handheld computing devices, PDAs, or webservers, whereby the software required for computing the analysis result may reside on the computing device, be downloaded upon activation of the device or downloaded for each analysis. The latter is particularly advantageous when the computing, device is connected to multiple card readers for different tests respectively requiring different signal analysis procedures. General purpose computing devices are readily available as off-the shelf components at a much lower capital cost than the special purpose computing modules used in conventional analyzers. This reduces the overall cost of the system of the invention, even when the general purpose computer is connected with only one card reader unit, such as may be the case in a portable embodiment of the present system as discussed further below. The capital cost for the system of the present invention can be further reduced when the general purpose computing device is a device already in use for other purposes but with sufficient unused computing capacity to carry out the analysis function in accordance with the invention. Examples are existing departmental or central computers and servers in a hospital setting, or laptops and PDAs used at the point of care. Thus, simply using a general purpose computer in contrast to a special purpose microprocessor or computing module already renders the system of the invention more economical than prior art analyzers including such specialized hardware.

In a preferred embodiment of the invention, card readers with analog sensory output are connected to a laptop through a PCMCIA DAQ card. This embodiment is appropriate when multiple readers are connected to a general-purpose computer located within a hospital department, or when the card readers and computer are physically co-located as part of a mobile measurement system. Such a portable system is a compact, bedside blood analysis device that could stay at the patient-side as the patient is moved from location to location within a hospital. Moreover, such a portable system is advantageous over the existing specialized analyzer units, since the single general purpose computer (the laptop in this case) can be integrated with a multitude of different card readers for specialized diagnostic cards, each being used for a different, very specific point of care test, whereby the capital cost for multiple card readers is significantly lower than for multiple self-contained analyzers.

In another embodiment of the system of the invention, one or more card readers are connected to a general-purpose computers the card readers being located at remote point-of-care blood testing locations within a healthcare institution. The card readers are connected to the computer through a data acquisition interface and by wire or a radio frequency connection.

It is another object of this invention to teach different physical arrangements of card-reader and data acquisition interface depending on the specific use of the system.

Another object of this invention is to provide cost-effective electronic quality control elements and software for the point-of-care blood analysis system.

It is a further object of this invention to teach a point-of-care blood analysis system that cost-effectively provides quality assurance through consolidation of the analysis operations and the supporting software into a single computer for processing sensor data from a multitude of low cost card readers connected thereto. Since the distributed components in the system of the invention are significantly less expensive than the currently used distributed analyzer units, the system of the invention provides for a much more economical set-up with the desired low cost bedside components. This allows the distributed components to be permanently installed at the bedside location and obviates the need for transportation and tracking of mobile units.

It is another object of the invention to teach a cost-effective integration of point-of-care blood analysis technologies. This objective is met in a system consisting of one or more card readers for connection to a general-purpose computer. The card reader contains one or more receptacles or connectors, each for engagement with its own family of diagnostic cards, wherein some of the individual test cards and read-out receptacles are based on different sensor technologies. This allows the card readers and in fact the whole system to be used for a variety of bedside diagnostic tests, thereby obviating a number of different analyzer units currently used. This significantly reduces capital cost and operating cost. Finally, by centralizing the analysis of the sensor data in the central computer rather than the distributed components, not only quality assurance cost are lowered, but also personnel training cost, since the personnel conducting the sample collection no longer need to be trained on all aspects of operating a complete analyzer.

BRIEF DESCRIPTION OF THE DRAWINGS

The invention will now be further described by way of example only and with reference to the following drawings, wherein

FIG. 2B is a top view of the electrode module and measurement region of the diagnostic card shows in FIG. 2A;

FIG. 2C is a cross-section through the electrode module and measurement region of the diagnostic card taken along line A–A' of FIG. 2B.

FIGS. 4A–4D are block diagram schematics illustrating the possible locations of major components of the point-of care blood analysis system of this invention.

DETAILED DESCRIPTION OF THE PREFERRED EMBODIMENTS

Figure 1:
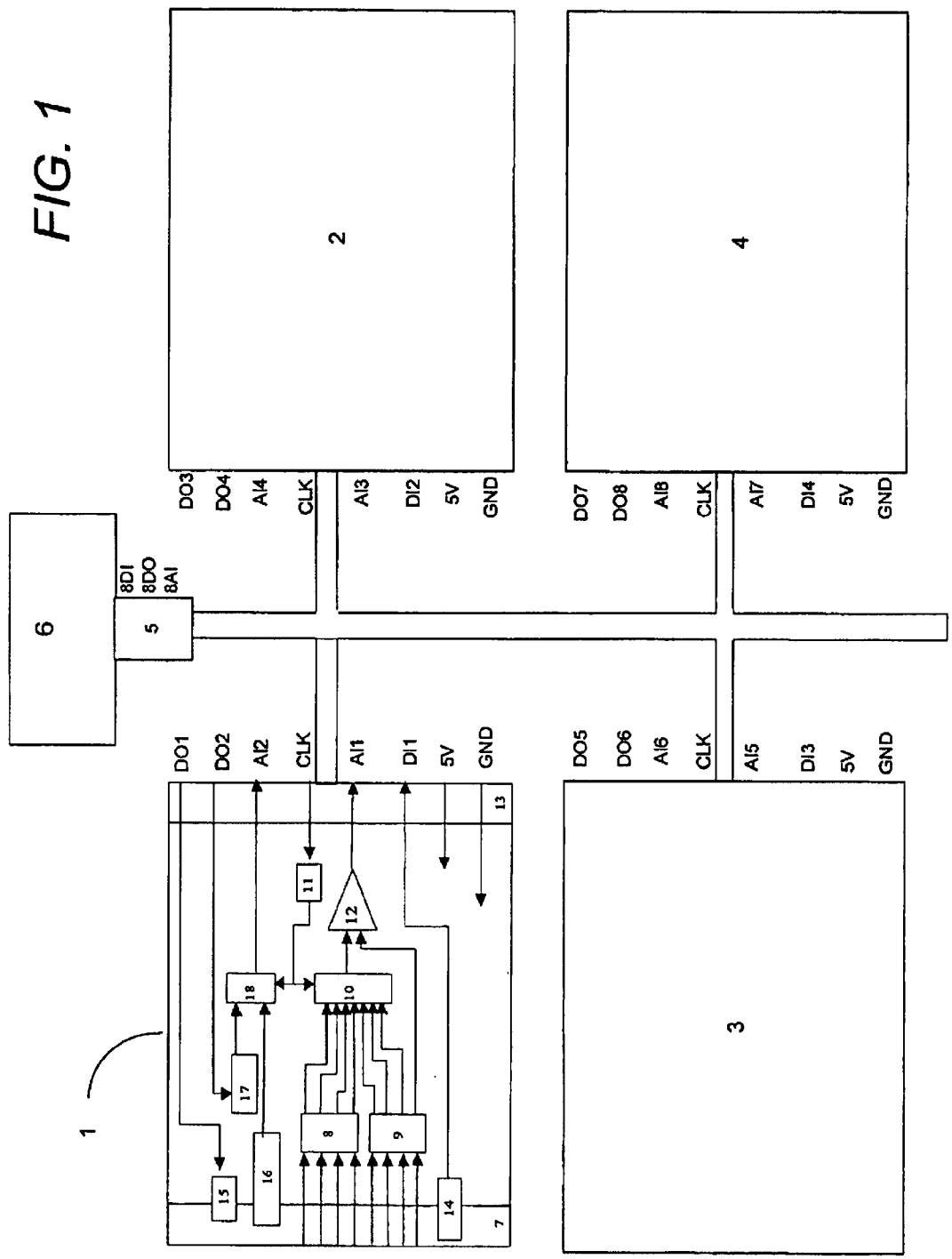
FIG. 1 is a block diagram and circuit schematic of a preferred embodiment of the point-of-care diagnostic system in accordance with this invention.

FIG. 1 is a block diagram of a preferred embodiment of a point-of-care in-vitro blood analysis system in accordance with the invention The blood analysis system according to this embodiment of the invention consists of an array of card readers 1–4 for connection to a general-purpose computer. The card readers and companion diagnostic cards are based on modified smart-card and smart-card connector technology. The four card readers 1–4 are connected through a single DAQ card 5 to a general-purpose computer 6. In this specific embodiment, the card readers have multiplexed analog sensor signal outputs. The general-purpose computer is a commercial laptop personal computer, and the DAQ card, also an off-the-shelf component is a National Instruments DAQ card. This DAQ device is a PCMCIA card that plugs into the laptop's PCMCIA socket. It accommodates up to 16 analog inputs. There are only eight analog inputs (8AI) shown in FIG. 1 because only eight channels are used in this embodiment. The DAQ accommodates eight digital inputs (8DI in FIG. 1) and eight digital outputs (8DO in FIG. 1). It can thus support the simultaneous operation of four card readers where the card reader's design requires up to two digital inputs and two digital outputs per card reader (eight readers requiring only one digital I/O per reader). Those skilled in the art recognize that there are many different off-the-shelf data acquisition products available. The physical configuration of such a circuit might be a PC card as used in this embodiment of the invention, and suitable for mobile configurations of the system, or a printed circuit board for rack mounting within a tabletop personal computer. Devices are available to support much larger analog input counts and many more channels of digital I/O for use in systems with many more card readers than the four described in this embodiment. In this embodiment, analog sensor signals are transmitted from each card reader to the computer. This is appropriate for relatively short transmission distances. A four card-reader system according to this embodiment therefore is useful as a distributed measurement system for installation within a unit of a hospital. The system according to this embodiment also is useful as a mobile in-vitro diagnostic device. The portable configuration of the diagnostic device of this embodiment includes a portable laptop and PCMCIA DAQ with one to four card-readers connected thereto. A mobile system with provision for four card readers is configurable as a low-cost integrated analyzer because it can accommodate for example up to four diagnostic card and card-reader technologies in a single general-purpose portable diagnostic device.

Figure 2A:
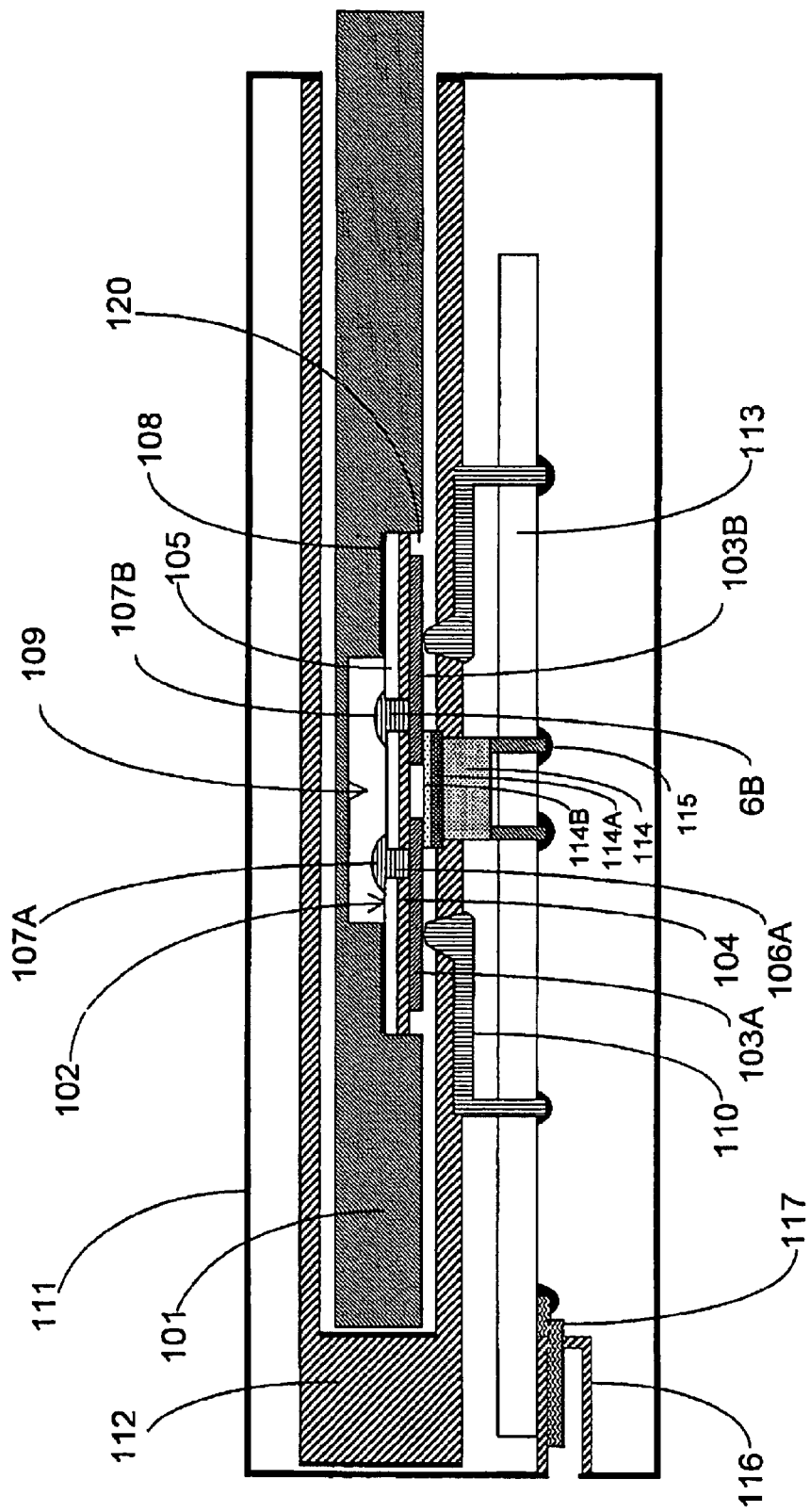
FIG. 2A is a schematic cross-section of a card reader with inserted diagnostic card of the system shown in FIG. 1.

FIG. 2A shows a cross-sectional schematic of a card reader with inserted diagnostic card according to the invention, which reader is part of the FIG. 1 embodiment of a point-of-care blood analysis system. FIG. 2A shows a card reader with a housing 111 containing a modified smart-card connector with plastic body 112. The schematic shows a diagnostic card with a plastic card body 101 inserted into the connector as it would be during the use of the diagnostic card and card reader.

The specific construction of the diagnostic card is not part of the present invention and is described in greater detail in co-pending application Ser. No. 09/871,821. The diagnostic card as shown in FIG. 2A is preferably a device that uses components with standard geometries from electronic smart-card technology with modifications to result in a card with an electrochemical sensor array and fluidics. Any diagnostic card which can produce a raw analog sensory output representative of a species concentration in the sample can be used in the system of the invention, as long as the construction of the card and the card reader allows for transmission of the raw sensory signal produced by the card to the card reader. The preferred diagnostic card includes an electrode module 102 embedded in the card body 101. The card body is a thin plastic similar in shape and size to a smart card or a credit card. The card body contains a module cavity 120, appropriate in size to accept the electrode module, and additional other measurement and reservoir chambers, openings suitable for introduction of fluids including the sample fluid and conduits or channels for movement of fluids within the card body for the purpose of performing an intended blood analysis procedure within the device and for producing an analog sensory output. These other chambers, reservoirs and channels are collectively known in the art as fluidics. The specific configuration of the fluidic elements within the card depend on the specific type of blood analysis being performed by the card. Some cards may for example incorporate a calibrator, other card types a fluid reagent, still others incorporate no on-board calibrator or reagent. The configuration of channels connecting orifices and reservoirs to the measurement chamber, depends on the sequence of the fluid manipulation steps within the card which also depend on the type of blood analysis. As described in copending application Ser. No. 09/871,821, the diagnostic card has at least a measurement chamber 109 (see FIG. 2A), which is the region of the card where the measurement takes place, and at least an orifice for introduction of a sample into the card, not shown in the diagram. The electrode module 102 includes the same chip carrier as used to hold the chip in the conventional electronic smart-card applications. However, in this construction, the chip-carrier is primarily used as an electrode carrier. The chip-carrier is die-cut from a substantially planar sheet consisting of a laminated bi-layer of a metal 103 and an insulator 105 with an optional adhesive layer 104 therebetween. The electrode module 102 further includes at least two electrodes as will be described in more detail below. The electrode module 102 is sealed in the module cavity 120 by a seal 108. The insulator 105 includes electrode openings 106A and 106B which extend therethrough and define the location of the two electrodes of the module. The metal layer 103 is spatially divided into two separate metal elements 103A, 103B. Each metal element extends over a region beyond the electrode openings 106 to a location at which contact can be made to an external circuit on circuit board 113 (as will be described in more detail below) by engaging contacting elements 110 on the outer surface of the electrode module 102. At the electrode openings 106A and 106B the insulator layer 105 is respectively coated with one or more thin film over-layers or membrane layers 107A, 107B of electrochemical material which extend through the openings and into electric contact with that portion of the metal element 103A, 103B respectively surrounding the opening. That portion of the metal element and the respectively contacting membrane 107 together form an electrode. Electrochemical materials which can be used for these membranes are well known in the art and include immobilized electrolytes and ion selective membranes in ion sensors, bio-layers containing enzymes in enzyme electrodes and other related bio-sensors, immobilized electrolytes and gas permeable layers in gas sensing electrodes. The membranes 107 impart chemical sensitivity to the electrodes that are preferably used for sensing. In such an electrochemical cell with a pair of electrodes, one electrode will usually generate an electrical signal in proportion to a species concentration. That electrode is called the sensor or working electrode. The other electrode is called the reference electrode. Electrode modules of this embodiment typically will have 6 or 8 electrodes in total, in a geometric arrangement specified by relevant ISO standards for electronic smart-cards. An 8-electrode arrangement is shown in top view in FIG. 2B.

The card reader's connector is a modified version of a device used for smart-card connection within a smart-card reader. Smart-card connectors as part of smart-card readers are known to a person skilled in the art. Smart-card connectors according to ISO standard specifications can have 8 contacting pins 110 in two rows of 4, as shown in FIG. 2B. They can be used to make contact to diagnostic cards with 6 or 8 pin electrode modules whose dimensions conform to ISO specifications (ISO 7816 2) for smart cards. The contacting elements 110 are retained within the connector device and embedded in its plastic body 112 as is apparent from FIG. 2A. They also traverse the circuit board 113 generally found in smart-card readers and extend through holes therein, with solder connections 115 being made to circuits on the surface of circuit board. Smart-card connections of the art also contain a mechanical on/off switch with electrical pins also traversing the connector body and circuit board. The switch is not shown in FIG. 2A. The mechanical switch makes or breaks an electric contact when a card is inserted into the connector. The circuit board 113 generally also contains other electronic components of the signal conditioning circuitry also shown in FIG. 1, as well as the I/O connector (not shown in FIG. 2A) for connection to a data acquisition interface.

In use, sample fluid is collected into the diagnostic card body through its sample acquisition orifice and is positioned over the electrodes of the electrode module in the measurement chamber 109. The diagnostic card is then inserted into the connector slot of the card reader. Depending on the specific test card type the order in which the sample is acquired and the card is inserted into reader may differ. The diagnostic card, with its precisely located metal elements 103A, 103B of the electrode module 102, is engaged to the connector device so that the metal elements come into electrical contact with contacting elements 110 of the connector device. An electrical signal is developed at the electrodes when sample fluid within the measurement chamber comes into contact with sensor membranes 101 over the electrode openings 106. Those skilled in the art will appreciate, for example, that an analog signal in the form of a change in electrical current, voltage or conductance could be measured at the electrodes in relation to a chemical concentration in the sample fluid. This analog signal, after amplification and multiplexing within the card reader as described below, is then evaluated by a general-purpose computer using specific software installed thereon, as will be explained later. Other operations may also be performed in the chemical analysis procedure using a diagnostic card. Operations such as calibration and addition of reagent are often performed within fluidic housings of analytical devices.

It is well known in the art of in-vitro diagnostics that certain measurements require accurate control of the measurement temperature to achieve the necessary accuracy of the chemical analysis. This is the case for blood gas measurements, enzyme activity assays, coagulation time measurements and the like. FIG. 2A and FIG. 2B show how thermal control elements are incorporated into the modified smart-card connector's plastic body. Each of the thermal control elements, the heater chip 115 and the thermal sensor 118, are mounted on a copper heater block 114A with insulating film coating 114B embedded in the plastic body of the smart-card connector. They are mounted so that the heater block's top surface is parallel to the diagnostic card body and lies in contact with it upon insertion of the card into the connector. The heater block is positioned so that it contacts the diagnostic card in the measurement region. Thus, in the smart-card connector they are located between the contacting ends of the two rows of contact pins 110 as shown in FIG. 2B. The electrical connection pins 115 of heater 114 and pins 119 of the thermal sensor 118 on the lower surface of the respective thermal elements traverse the plastic connector body 112 and the circuit board 113. They are solder-connected to circuitry on the circuit board as shown in FIG. 2A. The approximate relative dimensions of a chip-based thermal sensor, shown in the plan view of FIG. 2B, correspond to a specific embodiment of the device using an off-the-shelf LM35 thermal sensor chip. The heater is a ceramic chip resistor in this embodiment. Those skilled in the art will recognize that there are numerous other choices for thermal sensors such as thermistors and RTD's. Moreover, other circuit elements are available for use as heaters such as diodes and power transistors and those with appropriate physical dimensions could also be used in this embodiment.

Referring to FIG. 2A, the raw analog sensor signals collected from the diagnostic card through the connector pins 110 are buffered by operational amplifiers on circuit board 113. On the electrical schematic of FIG. 1 the same sensor signals are shown passing through the connector 7 and terminating at two quad operational amplifiers 8 and 9. These operational amplifiers can be configured as voltage followers or current to voltage converters depending on whether the raw sensor output is a voltage or a current. The buffered signals are multiplexed onto a single channel using a multiplexer 10, switched by counter 11. Multiplexed signals are then amplified by the instrumentation amplifier 12 and connected to the first analog input, A1, of the DAQ via I/O connector 13. The smart-card connector's mechanical switch 14, the position of which indicates the presence of a diagnostic card in the smart-card connector, is connected to the digital input of the DAQ. This signal informs the computer of the beginning of a measurement. The DAQ also provides ground, power supply (5V supply), and a clock signal to synchronize the card reader's multiplexers with the DAQ.

One digital output, DO1, from the DAQ is connected to module 15 including the heater and its power circuit, switching the heater on and off. The thermal control of the measurement in the card reader of this embodiment is performed by software in the general-purpose computer and not in the card reader. This allows a much simpler construction for the card reader and reduces the unit cost to a fraction of that of conventional bedside distributed diagnostic units. The temperature of the measurement zone is acquired by module 16, the thermal sensor including amplifier circuit. The amplified raw voltage signal from the thermal sensor is multiplexed into other channels of the card reader in a second multiplexer 18 and transmitted to the second analog input, AI2 of the DAQ. The computer's software converts the raw thermal signal to temperature using stored calibration factors, then compares the temperature to a set point, the difference being used to calculate how to regulate the heater, as is well known in the field of control. In a particularly simple implementation, the regulating signal is an on/off switch provided to the card reader by the DAQ digital output, DO1, under computer software control. In blood gas measurements it is important to ascertain the atmospheric conditions and especially atmospheric pressure. Conventional blood gas systems therefore incorporate pressure sensors as well as thermal sensors into each analyzer. In the system according to the invention, a single pressure sensor can be incorporated into the general-purpose computer, or local atmospheric pressure data can be down-loaded from an internet source by the computer, again eliminating costly components from the bedside unit.

The card reader further preferably contains a quality control subsystem identified as quality module 17 that is activated by the computer through a second digital output, DO2. When prompted, quality module 17 collects quality control signals for output to the computer through a second analog input AI2 to the DAQ. The quality control signals are multiplexed with the thermal sensor signal by multiplexer 18. FIG. 1 shows only a single channel of quality control signal, but the number can be much larger, determined by the number of multiplexer channels designed into the circuit. In this embodiment two multiplexed analog channels AI1 and AI2 are transmitted by each card reader, one channel for analytical sensors, one channel for control signals. This is because two analog inputs to the DAQ are available per card reader. In certain situations it might be advantageous to multiplex all of the analog outputs onto one channel. This is clearly feasible with a different circuit arrangement of multiplexers.

In general, the quality control system as part of the point-of-care blood analysis system according to the invention consists of a hardware component in the card reader and a software component in the computer. The hardware components are sensing and electronic structures, either within the card reader itself for generating quality control signals from the reader and diagnostic card and/or in an electronic simulator device inserted into the card reader as is known in the art. Quality control signals are transmitted to the computer wherein the software analyzes the quality control signals to generate quality control data. Two kinds of quality control data are available: those taken during a measurement and those taken between measurements. Those taken during a measurement will control the quality of processes occurring while a diagnostic card with blood sample is inserted into the card reader. These are the fluidic processes, sensing processes and card-heating processes. Quality control data can be acquired between measurements, continuously, programmed intermittently, or by a user command generated at the general-purpose computer. The quality control data thus obtained is useful information for the quality supervisor and can provide the user go/no-go decisions on the measurement procedure. The software in the general-purpose computer can detect non-conformance of the quality data during a measurement, abort the measurement and output an error signal. It can detect non-conformance between measurements, then thereafter output an error signal and disable the use of the card reader until the non-conformance has been corrected.

Figure 3:
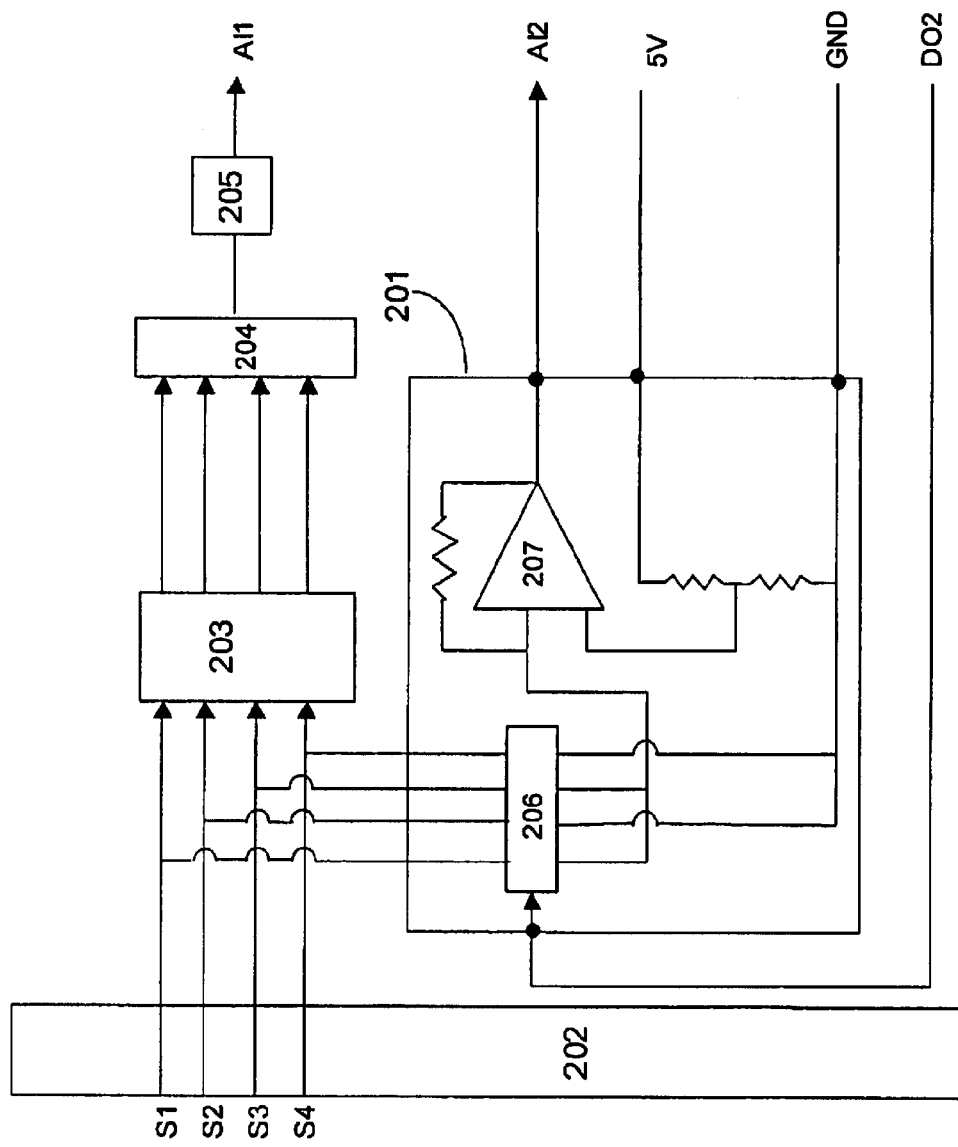
FIG. 3 is a circuit schematic of a quality control subsystem of the point-of-care blood analysis system according to the invention.

A specific embodiment of a quality control sub-system is shown in FIG. 3. This quality control sub-system 201 monitors the electrical integrity of the connector device 202 when connected to an array of potentiometric sensors. The electrical integrity of the connector is an important quality factor. Because the card reader is used in an environment where blood and other fluids can be splashed there is a clear opportunity for error if blood contaminates connector surfaces and causes electrical leakage. For proper operation of the measurement system there should be minimal leakage current from a connector pin. The effective resistance to ground of a connector pin should be significantly larger (about 100 times at least) than the analytical sensor's resistance (which is about 1E8 in the electrodes of this diagnostic card technology), as is well known in the art. Shown in FIG. 3 is a connector 202. There are four analytical sensor channels, S1–S4, received by the connector from potentiometric sensors on the diagnostic card. Sensor channels from the connector are connected to a quad op-amp buffer 203 whose outputs are connected to multiplexer 204, then output amplifier 205 to the output terminal for connection to the analog input, AI1 of the DAQ which is not shown. An electronic switch array 206 is also connected to the four sensor channels from the connector. On the other side of the electronic switch, alternate sensor channels (corresponding to alternate connector pins) are connected to a voltage source or a current-to-voltage converter 207 whose output is ultimately connected to a second analog input AI2 to the DAQ. Under remote computer control a digital output, DO2 from the DAQ toggles the electronic switch. In the open position the resistance of the switch 206 is high. This component is chosen so that its open resistance is more than 100 times larger than the resistance of the analytical sensors on the diagnostic card (greater than 1E10 ohms). With the switch 206 closed, current flows between adjacent pins if there is leakage. This quality control of the connector leakage is appropriate for potentiometric sensors wired to op amp buffers. For amperometric sensors, which are themselves connected to a current to voltage converter, the background current in the absence of a diagnostic card indicates leakage current. Those skilled in the art will recognize that many other circuit designs are effective in testing the connector pin's isolation.

Another quality control sub-system verifies proper operation of the thermal controller. This may require additional thermal sensors: one to monitor ambient temperature away from the heated zone, another on the other side of the connector to monitor heat flow through the diagnostic card. An electronic simulator for connection to the smart card connector containing thermal elements could be effective for quality control of the card reader's thermal sub-system.

A generalized description of the components of the point-of-care in-vitro diagnostic system of the invention is shown in the block diagram of FIG. 4A. One or more card readers 303 for reading diagnostic cards 304 are connected through a data acquisition interface 302 to a general-purpose computer 301. The computer is connected to a network 300.

Diagnostic cards 304 are unit-use devices containing sensors 318 and fluidics 319. In one embodiment of the invention sensors are electrochemical electrodes. However, in a generalized scheme, diagnostic cards can be based on other analytical methods known in the art, such as optical methods, for example absorbance, fluorescence or luminescence. The sensor 318 is understood to be a molecule or molecules in the measurement region of the diagnostic card that absorbs light fluoresces or luminesces, this optical response being related to the chemical concentration of a species being analyzed.

The card readers 303 contain devices 313 that engage the diagnostic card. In the electrochemical embodiment these are preferably smart-card connectors. The card readers contain signal-conditioning circuits 314, but can also contain a thermal control sub-system 315, mechanical on/off switch 316 and quality control sub-system 317. Optical card readers may contain optical subsystems including light emitting diodes, lasers, detectors and the like.

Data acquisition interfaces 302 generally contain an A/D converter 309, multiplexer 310, digital I/O 311, and possibly a signal conversion device 312 such as a radio frequency wireless transmitter or a RS232 wire transmitter.

The general-purpose computer 301 is a tabletop personal computer, a laptop or a hand-held computing device such as a PDA. The computer's software includes software 305 to drive the data acquisition interface, software 306 to control the measurement (particularly thermal control software, but possibly also software to control fluidic processes), software 307 for quality control and software 308 to calculate concentration values from sensor signals.

The physical relationship of the major components of the point-of-care in-vitro diagnostic system of the invention is shown in the block diagram of FIGS. 4B–4D. Systems with two card readers are shown to illustrate the flexibility of the system to accommodate multiple card readers.

FIG. 4B shows a simplified block diagram of the embodiment described above and illustrated in FIGS. 1–3. Box 320 depicts computer 301 and data acquisition interface 302 as a single physically connected entity. In one example 302 is a DAQ printed circuit board mounted inside a personal computer, in another example it is a DAQ card slotted into a PCMCIA slot of a laptop. The card readers are remote from the computer and data acquisition interface.

In another embodiment shown in FIG. 4C the data interface 302 and one or more card readers are integrated into a housing 321. This in turn engages the computer 301, for example through a PCMCIA slot. The combination of computer, data acquisition interface and card reader are now part of a single, physically connected entity. This embodiment is suited for a portable system.

In yet another embodiment shown in FIG. 4D the card reader transmitter 323 is an integrated combination of a data acquisition interface 302 and a card reader 303 in a single housing. In this embodiment the data acquisition interface contains a signal converter. The output from the card reader transmitter is a digital signal that can be transmitted over longer distances than an analog signal. The output might be a wireless-transmittable data stream (with the computer equipped with a receiver device as is known in the art) or a wire-transmittable data stream protocol such as RS232.

This invention contemplates the simple integration of diverse measurement technologies such as the optical and electrochemical technologies cited above. The integration process is as simple as the physical integration of two card different readers. All of the other components of the system are common and independent of measurement technology.

A dedicated visual display device for displaying measurement data at the point-of-care is not usually required in any of the remote card reader implementations. There are already display devices at or near the point-of-care that can access the measurement data from computer 301 through network 300. Point-of-care display devices may be on other point-of-care equipment that is network attached, on other network-attached personal computers at the point of care or on PDAs in radio frequency communication with a network.

Those skilled in the art will recognize that the smart-card connector and diagnostic smart card according to the invention could also be used in a conventional self-contained analytical instrument. By incorporating the invented connector and signal conditioning elements together with A/D converter, microprocessor, memory and display elements as they might be combined in a conventional self-contained analytical instrument of the prior art there results an improvement in compactness and cost-effectiveness of the product. A typical example of the components of a conventional instrument is described in U.S. Pat. No. 5,282,950.

I claim:

1. A point-of-care blood measurement system for performing in-vitro diagnostic chemical analysis of a sample, comprising
   a diagnostic card reader for receiving a raw sensory signal from a diagnostic card exposed to the sample and for providing an analog sensory signal directly related to the raw sensory signal, the raw sensory signal being dependant on a concentration of a chemical species in the sample,
   a data acquisition circuit for converting the analog sensory signal into a digital sensory signal; and
   a general-purpose computer separate and distinct from the diagnostic card reader for receiving and analyzing the digital sensory signal and producing an analysis result output representative of the chemical species concentration in the sample.

2. The system of claim 1, wherein the diagnostic card reader is a smart-card reader and the diagnostic card is a modified smart card.

3. The system of claim 1, wherein the diagnostic card reader includes amplification means for amplifying the raw sensory signal, and sensor multiplexing means for generating an output including secondary signals in addition to the raw sensory signal.

4. The system of claim 1, wherein the general-purpose computer is a portable computer and the data acquisition circuit is a personal computer data acquisition card, or a personal computer memory card international association data acquisition card inserted into the computer.

5. The system of claim 1, wherein the general-purpose computer is a personal computer and the data acquisition circuit is a data acquisition card incorporated therein.

6. The system of claim 1, wherein the diagnostic card reader and the data acquisition circuit are incorporated In the same housing.

7. The system of claim 1, wherein the system includes a plurality of diagnostic card readers and the data acquisition circuit is a data acquisition card constructed for converting the respective analog sensory signal of each one of the plurality of diagnostic card readers.

8. The system of claim 1, wherein the system includes a plurality of diagnostic card readers and a data acquisition circuit for each diagnostic card reader and the separate computer is connectable to all data acquisition circuits.

9. The system of claim 1, wherein the diagnostic card reader and the data acquisition circuit are distributed components of the system and the computer is a remotely located central component, the system further including communication means for electrical or electronic communication of the digital signal to the computer.

10. The system of claim 1, wherein the conversion of the digital sensory signal into an analysis result output is carried out in the general-purpose computer by way of a data-calculation software operating thereon.

11. The system of claim 1, further including measurement control means for controlling measurement conditions in the diagnostic card, the measurement control means including heating means positioned in the diagnostic card reader for heating a diagnostic card inserted therein, and control software on the general-purpose computer for controlling operation of the heating means.

12. The system of claim 1, further comprising quality control means for monitoring the quality of the raw sensory signal, which quality control means is implemented as quality-control software running only on the computer.

13. The system of claim 11, wherein the computer is constructed for providing at least one digital control signal to the diagnostic card reader for controlling the operation of the heating means.

14. The system of claim 1, wherein the diagnostic card reader includes a means for generating an on/off signal to the data acquisition circuit and general-purpose computer.

15. The system of claim 1, wherein the diagnostic card reader is constructed for receiving the raw analog signal from one of a number of different diagnostic cards each specific for a different chemical species in the sample, the raw analog sensory signal depending on a concentration of the respective different chemical species in the sample.

16. The system of claim 7, wherein the computer is constructed to provide a single clock signal to all diagnostic card-readers by way of the data acquisition unit.

17. The system of claim 13, wherein the heating means in the card reader is constructed to heat a measurement region of a diagnostic card inserted therein.

18. The system of claim 14, wherein the means for generating the on/off signal is a mechanical switch in the diagnostic card reader which is normally in the off condition and is actuated upon insertion of a diagnostic card into the diagnostic card reader.

19. A point-of-care blood measurement system for performing in-vitro diagnostic chemical analysis of a sample, comprising
   a diagnostic card reader for receiving a raw analog sensory signal from a single use blood diagnostic card exposed to the sample and for providing an analog output signal directly related to the raw sensory signal, the raw sensory signal being dependent on a concentration of a chemical species in the sample, sensor multiplexing means for generating a secondary output signal in addition to the analog sensory signal;

a data acquisition circuit for converting the amplified analog sensory signal into a serial digital sensory signal; and a general-purpose computer separate and distinct from the diagnostic card reader for receiving and analyzing the digital sensory signal and the secondary output signal and for producing an analysis result output representative of the chemical species concentration in the sample, the computer having an input port for connection to at least one data acquisition circuit.

20. A point-of-care blood measurement system for performing in-vitro diagnostic chemical analysis of a sample, comprising a diagnostic card reader for receiving a raw analog sensory signal from a single use blood diagnostic card and for providing an analog sensory output signal directly related to the raw sensory signal, the raw sensory signal being dependent on a concentration of a chemical species in the sample, the diagnostic card and the card reader further including fluidics for control and/or supply of the sample fluid and other reagents or calibrants or other fluids required for the sensory analysis of the sample;

amplification means for amplifying the analog sensory output signal and sensor multiplexing means for generating an output including signals in addition to the analog sensory output signal;

a data acquisition circuit for converting the analog sensory output signal into a serial digital sensory signal, and a signal conversion circuit for converting the digital sensory signal of the data acquisition circuit to a radio frequency digital signal; and a general-purpose computer for receiving and analyzing the radio frequency digital signal and producing an analysis result output representative of the chemical species concentration in the sample, the computer having a radio frequency receiver module for receiver module for receiving the radio frequency digital signal produced by the signal conversion means.

21. The system of claim 20, wherein the diagnostic card reader further includes a test circuit for quality control of the card reader and especially the interfacing thereof with the diagnostic card.

22. A card reader for use in a point-of-care blood measurement system for performing in-vitro diagnostic chemical analysis of a sample including a diagnostic card reader, a data acquisition circuit for converting an amplified analog sensory signal output by he card reader into a digital sensory signal, and a general-purpose computer separate and distinct from the diagnostic card reader for receiving and analyzing the digital sensory signal and producing an analysis result output, the card reader comprising:

a housing;

a connector for engaging a diagnostic card exposed to a sample and for receiving a raw sensory signal from the diagnostic card for providing an analog sensory signal directly related to the raw sensory signal, the raw sensory signal being dependent on a concentration of a chemical species in the sample; a signal conversion circuit for converting the analog sensory signal into a digital sensory signal directly related to the raw sensory signal; and a transmitter for wireless digital communication with the general-purpose computer for receiving the digital sensory signal from signal conversion circuit and transmitting the digital sensory signal to the computer.

23. The card reader of claim 22, wherein the diagnostic card is a modified smart card.

24. The card reader of claim 22, further comprising means for influencing the measurement conditions in a measuring region at an inserted diagnostic card, the means for influencing including a heating means for heating the measuring region and means for controlling the heating means, whereby the means for controlling is to located on the computer and the transmitter is a two way transmitter for transmitting the digital sensory signal to the computer and for receiving control signals from the computer for operation of the heating means.

25. The card reader of claim 23, further including fluidics for control and/or supply to the diagnostic card of the sample fluid and other reagents or calibrants or other fluids required for the sensory analysis of the sample.

26. The card reader of claim 23, wherein the diagnostic card and card reader are constructed to perform an optical measurement of the sample.

27. A card for use in a point-of-care blood measurement system for performing in-vitro diagnostic chemical analysis of a sample including a diagnostic card reader; and a general-purpose computer separate and distinct from the diagnostic card reader for receiving and analyzing the digital sensory and producing an analysis result output, the car reader comprising:

a housing;

a connector for engaging a diagnostic card exposed to a sample and receiving a raw sensory signal from the diagnostic card for providing a analog sensory signal directly related to the raw sensory signal, the raw sensory signal being dependent on a concentration of a chemical species in the sample; a signal conversion circuit for converting the analog sensory signal into a digital sensory signal directly related to the raw sensory signal;

and a transmitter for communication with the general-purpose computer, the transmitter being constructed for receiving the digital signal from the signal conversion circuit and producing a transmittable digital output signal for transmission to the computer through one of a wired connection and a wireless connection.

28. The card reader of claim 27, wherein the diagnostic card is a modified smart card.

29. The card reader of claim 28, further including fluidics for control and/or supply to the diagnostic card of the sample fluid and other reagents or calibrants or other fluids required for the sensory analysis of the sample.

30. The card reader of claim 27, further comprising means for influencing the measurement conditions in a measuring region of an inserted diagnostic card, means for influencing including a heating means for heating the measuring region and means for controlling the heating means, whereby the means for controlling is located on the computer and the transmitter is a two way transmitter for transmitting the digital sensory signal to the computer and for receiving control signals from the computer for operation of the heating means.

31. The card reader of claim 27, wherein the diagnostic card and card reader are constructed to perform an optical measurement of the sample.

* * * * *

UNITED STATES PATENT AND TRADEMARK OFFICE
CERTIFICATE OF CORRECTION

PATENT NO.     : 6,845,327 B2
DATED          : January 18, 2005
INVENTOR(S)    : Imants R. Lauks It is certified that error appears in the above-identified patent and that said Letters Patent is hereby corrected as shown below:

Column 4,
Line 2, delete "mere" and insert therefor -- there --;

Column 17,
Line 53, delete "he" and insert therefor -- the --;

Column 18,
Line 9, delete "at" and insert therefor -- of --;
Line 12, delete "to";
Line 29, delete "car" and insert therefor -- card --;
Line 34, delete "a" and insert therefor -- an --; and
Line 55, insert -- the -- between the words "card," and "means"

Signed and Sealed this

Tenth Day of May, 2005

JON W. DUDAS
*Director of the United States Patent and Trademark Office*